(12) United States Patent
Hreczuk-Hirst et al.

(10) Patent No.: US 9,102,714 B2
(45) Date of Patent: *Aug. 11, 2015

(54) POLYSIALIC ACID DERIVATIVES

(71) Applicant: Lipoxen Technologies Limited, London (GB)

(72) Inventors: Dale Howard Hreczuk-Hirst, London (GB); Sanjay Jain, London (GB); Peter Laing, London (GB); Gregory Gregoriadis, London (GB); Ioannis Papaioannou, London (GB)

(73) Assignee: Lipoxen Technologies Limited (GB)

( * ) Notice: Subject to any disclaimer, the term of this patent is extended or adjusted under 35 U.S.C. 154(b) by 336 days.

This patent is subject to a terminal disclaimer.

(21) Appl. No.: 13/650,048

(22) Filed: Oct. 11, 2012

(65) Prior Publication Data

US 2013/0144043 A1 Jun. 6, 2013

Related U.S. Application Data

(60) Continuation of application No. 12/717,073, filed on Mar. 3, 2010, now abandoned, which is a division of application No. 10/568,111, filed as application No. PCT/GB2004/003488 on Aug. 12, 2004, now Pat. No. 7,691,826.

(30) Foreign Application Priority Data

Aug. 12, 2003 (EP) .................................. 03254988
Aug. 21, 2003 (EP) .................................. 03255200

(51) Int. Cl.
| | |
|---|---|
| C07K 1/107 | (2006.01) |
| C07K 1/13 | (2006.01) |
| C08B 37/00 | (2006.01) |
| C07K 14/00 | (2006.01) |
| C07K 1/00 | (2006.01) |
| A61K 47/48 | (2006.01) |

(52) U.S. Cl.
CPC ............ *C07K 14/001* (2013.01); *A61K 47/4823* (2013.01); *A61K 47/48369* (2013.01); *C07K 1/006* (2013.01); *C07K 1/1077* (2013.01); *C07K 1/13* (2013.01); *C08B 37/00* (2013.01); *C08B 37/0006* (2013.01)

(58) Field of Classification Search
None
See application file for complete search history.

(56) References Cited

U.S. PATENT DOCUMENTS

| | | | |
|---|---|---|---|
| 5,329,028 A | 7/1994 | Ashkenazi et al. | |
| 5,965,532 A | 10/1999 | Bachovchin | |
| 7,691,826 B2 * | 4/2010 | Hreczuk-Hirst et al. | ....... 514/49 |
| 2010/0016217 A1 | 1/2010 | Jain et al. | |
| 2010/0022443 A1 | 1/2010 | Jain et al. | |

FOREIGN PATENT DOCUMENTS

| | | |
|---|---|---|
| SU | 675053 | 7/1979 |
| WO | WO9222331 A1 | 12/1992 |
| WO | WO0187922 A2 | 11/2001 |

OTHER PUBLICATIONS

Hreczuk-Hirst et al., Preparation and properties of polysialylated interferon-a-2b, AAPS Annual Meeting (2002) Toronto, Canada, M1056.
Bendele, "Short Communication: Renal Tubular Vacuolation in Animals Treated with Polyethylene-Glycol-Conjugated Proteins," Toxicological Sciences, Apr. 1998, vol. 42, No. 2, pp. 152-157.
Brocchini, "Polymers in Medicine: A Game of Chess," Drug Discovery Today, 8, (2003) pp. 111-112.
Chamow, et al., "Conjugation of soluble CD4 without loss of biological activity via a novel carbohydrate-directed cross-linking reagent," The Journal of Biological Chemistry (1992) 267(22): 15916-15922.
Cheng, et al., "Accelerated Clearance of Polyethylene Glycol Modified Proteins by Anti-Polyethylene Glycol IgM," Bioconjugate Chemistry, 10 (1999) pp. 520-528.
Conover, et al., "Physiological Effect of Polyethylene Glycol Conjugation on Stroma-Free Bovine Hemogiobin in the Conscious Dog After Partial Exchange Transfusion," Artificial Organ, 21 (1997) pp. 369-378.
Epenetos, et al., "Program Proceedings, American Society of Clinical Oncology, 38th Annual Meeting" Proceedings of ASCO, Clinical Pharmacology (May 2002), vol. 21, No. 2186.
Gregoriadis, et al., "Polysialic acids: potential role in therapeutic constructs," Biotechnol. Genet. Eng. Rev. (1999) 16, pp. 203-215.
Gregoriadis, et al.,"Polysialic acids: potential in improving the stability and pharmacokinetics of proteins and other therapeutics," Cellular and Molecular Life Sciences (2000) vol. 57, pp. 1964-1969.
Hunter, et al., "Therapeutic synthetic polymers: a game of Russian roulette," Drug Discovery Today (2002) 7, pp. 998-1001.
International Search Report for PCT/GB2004/003488, mailed Nov. 11, 2004.
Jain, et al., "Polysialylated insulin: synthesis, characterization and biological activity in vivo," Biochim. Biophys. Acta (2003) 1622, pp. 42-49.
MacMillan, et al., "Selective in vitro glycosylation of recombinant proteins: semi-synthesis of novel homogeneous glycoforms of human erythropoietin," Chemistry and Biology, Current Biology (2001) 8(2): 133-145.
McGuire, et al., "The Structure and Chemistry of Colominic Acid," (1964), vol. 3, No. 2, pp. 247-251.
Written Opinion for PCT/GB2004/003488, mailed on Nov. 11, 2004.
International Preliminary Report on Patentability PCT/GB2004/003488, date completed Dec. 9, 2005.

* cited by examiner

*Primary Examiner* — Eric Olson
(74) *Attorney, Agent, or Firm* — One3 IP Management, P.C.; Dean G. Stathakis; Peter D. Weinstein

(57) ABSTRACT

A polysialic acid compound is reacted with a hetero-bifunctional reagent to introduce a pendant functional group for site-specific conjugation to sulfhydryl groups, for instance side chains of cysteine units in drugs, drug delivery systems, proteins or peptides. The functional group is, for instance, an N-maleimide group.

15 Claims, 2 Drawing Sheets

POLYSIALIC ACID DERIVATIVES

CROSS-REFERENCE TO RELATED APPLICATIONS

This application is a continuation of U.S. application Ser. No. 12/717,073, filed Mar. 3, 2010, which is a divisional of U.S. application Ser. No. 10/568,111, filed Jul. 13, 2006, now U.S. Pat. No. 7,691,826, which is the National Stage of International Application No. PCT/GB2004/003488, filed Aug. 12, 2004, which claims the benefit of European Application No. 03254988.3, filed Aug. 12, 2003, and European Application No. 03255200.2, filed Aug. 21, 2003. All applications listed in this paragraph are incorporated herein by reference in their entirety for all purposes.

BACKGROUND OF THE INVENTION

The present invention relates to polysialic acid derivatives which are useful for conjugation to drugs, proteins and peptides, or to drug delivery systems such as liposomes, having sulfhydryl groups, as well as to conjugated products process for synthesising the derivatives and the conjugates and novel synthetic intermediates.

The extended presence of drugs either within the vascular system or in extravascular use is often a pre-requisite for their optimal use. Many antibiotics and cytostatics for instance, as well as a variety of therapeutic peptides and proteins, and liposomes are removed from the circulation prematurely and before effective concentrations in target tissues can be achieved. The half lives of a number of short-lived proteins (for instance enzymes, cytokines, etc.) have been augmented by conjugating these to low poly(ethylene glycol). It appears that PEG molecules prolong the circulation time of proteins and particles by forming a cloud around their surface, thus sterically hindering interaction with factors responsible for their clearance. However PEG is non-biodegradable and accumulation of PEGylated proteins intracellularly may be undesirable especially on chronic use (Bendele, A., Seely, J., Richey, C., Sennello, G., Shopp, G., Renal tubular vacuolation in animals treated with polyethylene-glycol conjugated proteins, *Toxicological sciences,* 42 (1998) 152-157; Conyers, C. D., Lejeune, L., Shum, K., Gilbert, C., Shorr, R. G. L, Physiological effect of polyethylene glycol conjugation on stroma-free bovine hemoglobin in the conscious dog after partial exchange transfusion, *Artificial organ,* 21 (1997) 369-378).

We have described the conjugation of a polysaccharide comprising 2→8 and or 2→9 (e.g., alternating 2→8 and 2→9) linked sialic acid units conjugated to proteins to increase their half life, reduce their immunogenicity/antigenicity or increase the stability of a variety of proteins. In WO92/22331, polysialic acids are reacted with a model drug and shown to extend the half life in the circulation of mice. In *Cell. Mot. Life Sci.* 57 (2000) 1964-1969 and in *Biotechnol. Genet. Eng. Rev.* 16 (1999) 203-215, Gregoriadis, et al., describe the conjugation of polysialic acids to asparaginase and catalase, and show that the clearance rates from circulation reduced whilst enzyme activity was retained. We have also polysialylated insulin (*Biochim. Biophys. Acta* 1622 (2003) 42-49 and shown it to be active. We have also polysialylated interferon (AAPS Annual meeting 2002, Toronto, Canada, M1056). We have also polysialylated antibody fragment Fab (Epenetos, A., et al., Proceedings of ASCO (*Clinical Pharmacy*) 21 (2002) 2186).

In all of these publications, polysialic acid is rendered reactive, by generating an aldehyde group at the non-reducing end by oxidation of the 7,8-vicinaldiol moiety with sodium periodate. The aldehyde group was then reacted with primary amine groups on proteins, generally assumed to be epsilon-amino groups of lysine moieties of the protein or N-terminal amine groups. The reaction forms a Schiff base which is reduced by cyanoborohydride to a secondary amine.

In WO-A-01/87922 we also suggest that derivatisation with other molecules could be carried out in the presence of denaturant to achieve increased levels of derivatisation. Examples of other derivatising agents are polyethylene glycol compounds. Activated PEG compounds such as tresyl-PEG and succinimidyl succinate ester of PEG were mentioned. The examples used succinimidyl succinate activated PEG, which is believed to react with amine groups.

PEG derivatives having functional groups for coupling to thiol groups are commercially available. The functional groups may be maleimide, vinyl sulfone, iodoacetamide or orthopyridyl disulphide groups. Since these reagents react specifically with cysteines, and since proteins have fewer cysteines on their surfaces than lysine groups, the derivatisation is more controllable. Furthermore, in the absence of a free cysteine in a native protein, one or more free cysteines may be added by genetic engineering. The advantage of this approach is that it makes possible site-specific derivatisation at areas on the protein which will minimise a loss in biological activity.

PEGylated proteins have been found to generate anti PEG antibodies that could also influence the residence time of the conjugate in the blood circulation (Cheng T, Wu, M., Wu, P., Chem, J, Roffer, S R., Accelerated clearance of polyethylene glycol modified proteins by anti-polyethylene glycol IgM, *Bioconjugate chemistry,* 10 (1999) 520-528. Despite, the established history of PEG as a parenterally administered polymer conjugated to therapeutics, a better understanding of its immunotoxicology, pharmacology and metabolism will be required (Hunter, A. C, Moghimi, S. M., Therapeutic synthetic polymers: a game of Russian Roulette. *Drug Discovery Today,* 7 (2002) 998-1001; Brocchini, S., Polymers in medicine: a game of chess. *Drug Discovery Today,* 8, (2003) 111-112).

It would be useful for modification by polysialic acid to be targeted towards thiol (sulfhydryl) groups. It would also be desirable for the efficiency of derivatisation by sialic acid to be increased, the processes described in our prior art mentioned above requiring high excesses of active polysialic acid. It would also be desirable to avoid the use of cyano borohydride.

BRIEF SUMMARY OF THE INVENTION

According to the present invention there is provided a novel compound comprising a polysialic acid having a moiety linked at one or each terminal unit which includes a functional group selected from N-maleimido groups, vinylsulphone groups, N-iodoacetamide groups and orthopyridyl disulphide groups.

The terminal unit to which the moiety is linked may be at the non-reducing end of the polysialic acid or at the reducing end of the polysialic acid. Generally the terminal sialic acid unit has been subjected to a preliminary chemical reaction to generate useful functional groups to which a maleimide-group containing reagent may be linked. We have found it convenient to use the chemistry disclosed in our earlier publications in which an aldehyde group is generated, as a preliminary step to generate the functional group via which the maleimide moiety may be linked.

In our earlier publications mentioned above, it is the non-reducing terminal unit which is converted into an aldehyde moiety by oxidation of the 7,8-vicinal diol moiety with sodium periodate to form the carbon 7-aldehyde compound. This is an appropriate reaction for the present invention.

As an alternative, it is possible to provide the aldehyde moiety at the reducing terminal unit. In this case, it is preferred (but is not essential) to carry out a preliminary step in which the non-reducing end is deactivated, by preliminary oxidation and reduction steps. A first reduction step converts the ketal unit at the reducing end into a reduced ring opened form, having vicinal diols. The vicinal diols are subsequently oxidised using sodium periodate to form an aldehyde moiety at the carbon atom previously forming the 7-carbon of the reducing terminal unit. Where the non-reducing terminal glycosyl (usually sialic acid) is not deactivated by a preliminary oxidation step, the terminal unit will be simultaneously activated.

DETAILED DESCRIPTION OF THE INVENTION

Figure 1:
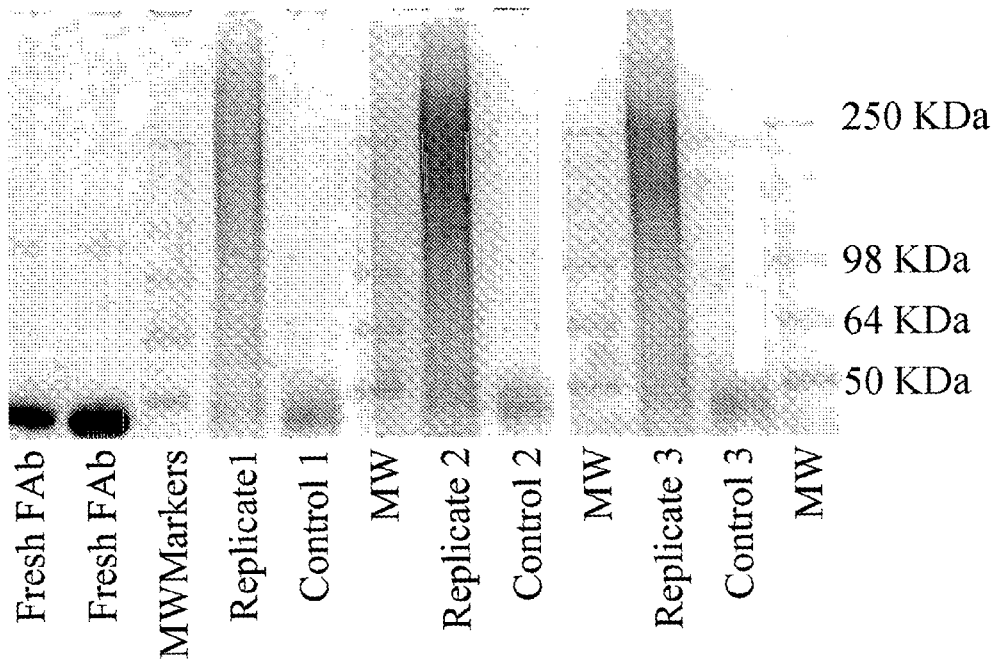
FIG. 1 shows an SDS-PAGE gel of triplicate samples of the conjugate of colominic acid maleimide (CAM) with Fab and relevant controls.

In the invention, the moiety which includes the functional group may be linked directly to the polysialic acid unit or, more conveniently, may be linked via a difunctional organic group, such as an alkane diyl group, an arylene group or an oligo(alkyleneoxy) alkane group, or alternatively an oligo peptidyl group. The linkage to the polysialic acid (from the linker or the moiety including the functional group may be a secondary amine, a hydrazone, an alkyl hydrazine an ester or a peptidyl group. The moiety may be generated by reaction of a polysialic acid substrate with a heterobifunctional reagent. The process forms a further aspect of the invention.

Reagents useful for introducing the selected functional groups are commercially available. A compound which will introduce a maleimide group onto an amine moiety without introducing any additional linker moiety is N-methoxy-carbonyl-maleimide. Generally the reagents include a second functional group for reaction with a group on the polysialic acid which may be the aldehyde group described above, or an amine group. Suitable second functional groups include N-hydroxy succinimide esters and their sulfosuccimide analogues and hydrazides. Preferably the compound is a N-maleimido-alkanoic acid hydrazide or an N-maleimidoarylalkanoic acid hydrazide, i.e., a compound having the general formula X—R—Y in which:

X is a N-maleimido, N-iodoacetamido, S-vinylsulphonyl or S-orthopyridyldisulphide group, R is alkane-diyl, arylene or aralkylene alkarylene, alkylene-oxaalkylene, or alkylene-oligooxa-alkylene or alkyl-oligopeptidyl-alkyl group; and Y is a hydrazide, amine or N-hydroxysuccinimide group.

Preferably R is $C_{1-6}$alkanediyl, $C_{2-3}$-alkyl-oxa-$C_{2-3}$-alkylene, $C_{2-3}$ alkyl-oligo(oxa-$C_{2-3}$ alkylene), or $C_{2-6}$ alkylene phenyl. Preferably X is N-maleimido or orthopyridyldisulphide. Preferably Y is a hydrazide or a hydroxyl succinimide.

Compounds which may be reacted with an aldehyde group, and which include a linker moiety and introduce a maleimide group include N-[(β-maleimidopropionic acid]hydrazide and 4-(4-N-maleimidophenyl)butyric acid hydrazide. The hydrazide group reacts with the aldehyde to form a stable hydrazone group. A suitable heterobifunctional compound which includes an oligo(ethyleneoxy)ethylene group is a compound comprising a polyethylene glycol (poly(ethyelenoxy)) group with, at one end, N-hydroxy succinimide (NHS) group and at the other end the functional group. The NHS group reacts with amine groups to form stable amide linkages. Heterobifunctional polyethyleneglycols with NHS at one end and either vinylsulphone or maleimide at the other end are available. Other examples of heterobifunctional reagents include, 3-(2-pyridyldithio)propionyl hydrazide, N-succinimidyl-3-[2-pyridyldithio]propionate, succinimidyl-H-[N-maleimidomethyl]cyclohexane-1-carboxylate), m-maleimidobenzoyl-N-hydroxysuccinimide ester, N-succinimidyl-[4-iodoacetyl]amino benzoate, N-[gamma-maleimidobutyryloxy]succinimide ester, N-[epsilon-maleimidocaproyloxy]succinimide ester and N-succinimidyl iodoacetate. Other reagents are available from Pierce Biotechnology and Shearwater Corporation (polyethylene glycol-based).

Sialic acids (also known as nonulosonic acids) are members of a family of amino containing sugars containing 9 or more carbon atoms. The most important of the sialic acids is N-acetylneuraminic acid (also known as 5-(acetylamino)-3,5-dideoxy-D-glycero-D-galacto-nonulosonic, lactaminic acid and O-sialic acid) which has the formula:

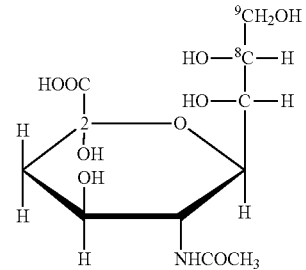

Polysialic acids may be linked 2→8 and/or 2→9, usually in the α-configuration. In some polysialic acids the linkages are alternating 2→8 and 2→9. The invention is also of utility for heteropolymeric polysaccharides comprising glycosyl units other than sialic acid units.

Polysialic acids are generally found to be non-toxic and substantially non-immunogenic. Furthermore the biodegration units, sialic acid, is not known to be toxic and, indeed sialic acids are widely found in animal proteins and cells, including blood cells and circulating proteins.

Polysaccharide compounds containing many sialic acid units are polysaccharides produced by *Escherichia coli, Moraxella nonliquifaciens, Pasteurella aeroginosis* and *Neisseria meningitidis* or derivatives thereof. For instance colominic acid derived (by hydrolysis to shorten the chain lengths) from *E. coli* K1 comprises α 2→8 linked sialic acid units. Polysaccharide from *E. coli* K92 strain comprises alternating 2→8 and 2→9 linked sialic acid units. Polysaccharide C of *N. meningitidis* group C has 2→9 linked sialic acid units.

One group of polysaccharide compounds which has been found to be of particular utility in the invention is group B polysaccharides. These compounds are produced by *N. meningitidis, M. nonliquifaciens, P. aeroginosis* A2 and *E. coli* K1. These compounds comprise a polysaccharide component comprising sialic acid residues and a phospholipid component. The sialic acid residues are linked (2→8)-α, the naturally occurring polymer consisting of about 200 residues. Some of the glycolipid molecules, especially the high molecular weight compounds appear to have a covalently attached phospholipid at the reducing end of the polysaccharide component.

It is preferable for the bacteria from which the polysaccharide compound is derived to be non-pathogenic for convenience during production. It is particularly suitable therefore for the polysaccharide to be derived from a non-pathogenic strain of *E. coli* such as *E. coli* K92 or, preferably, K1 which is non-immunogenic. *E. coli* K92 and K1 isolates are well-known and any such type of any such strains can be used as sources of suitable polysaccharide. Preferably the polysialic acid should have at least 2, preferably at least 5, more preferably at least 10, for instance more than 50 sialic acid units.

According to the invention, there is also provided a conjugate of a protein and the novel activated polysaccharide. The novel compound comprises a protein with at least one cysteine unit and, linked through a thioether bond to the side chain of a cysteine unit, a polysialic acid through a moiety joined at one or both terminal unit of the polysialic acid.

Where the polysialic acid derivative was a N-maleimido group the moiety will include a N-succinimidyl group, with the thioether linked at the α-carbon atom. Preferably the moiety also comprises a secondary amine, a hydrazone or an amide bond.

There is also provided in the invention a new process in which a polysialic acid is reacted with a heterobifunctional reagent having a first functional group for reaction with sulfhydryl groups and a second functional group different to the first group whereby the said second functional group reacts with a terminal unit of the polysialic acid to form a covalent bond therewith and form a capable of reaction with a sulfhydryl group functional polysialic acid.

In one embodiment the second functional group is a nucleophilic group, preferably hydrazine. This is of particular utility where the polysialic acid comprises an aldehyde group in the terminal unit whose carbonyl group is attacked by the nucleophilic group.

In another embodiment of the process the second functional group is electrophilic such as an N-alkoxyl carbonylimide such as N-hydroxysuccinimide ester or sulphosuccinimide ester, or carbodiimide. The terminal group in such cases is preferably nucleophilic such as amine.

In the process it is preferred that the reagent comprises a bifunctional organic group linking the first and second functional groups. Preferably the bifunctional organic group is selected from a $C_{2-18}$-alkanediyl group, an arylene group, an oligo peptide and an oligo(alkoxy)alkyl group.

Examples of suitable reagents are given above.

Most usefully the process involves a subsequent step in which the functional polysialic acid is reacted with a polypeptide or a protein having at least one free and unprotected Cys unit whereby the functional group forms a thioether linkage with the thiol group of a Cys unit to form a polysialylated polypeptide or protein. The process is particularly suitable where the protein contains a single Cys unit, whereby site-controlled derivatisation is achieved.

The invention is illustrated in the accompanying examples.

Example 1

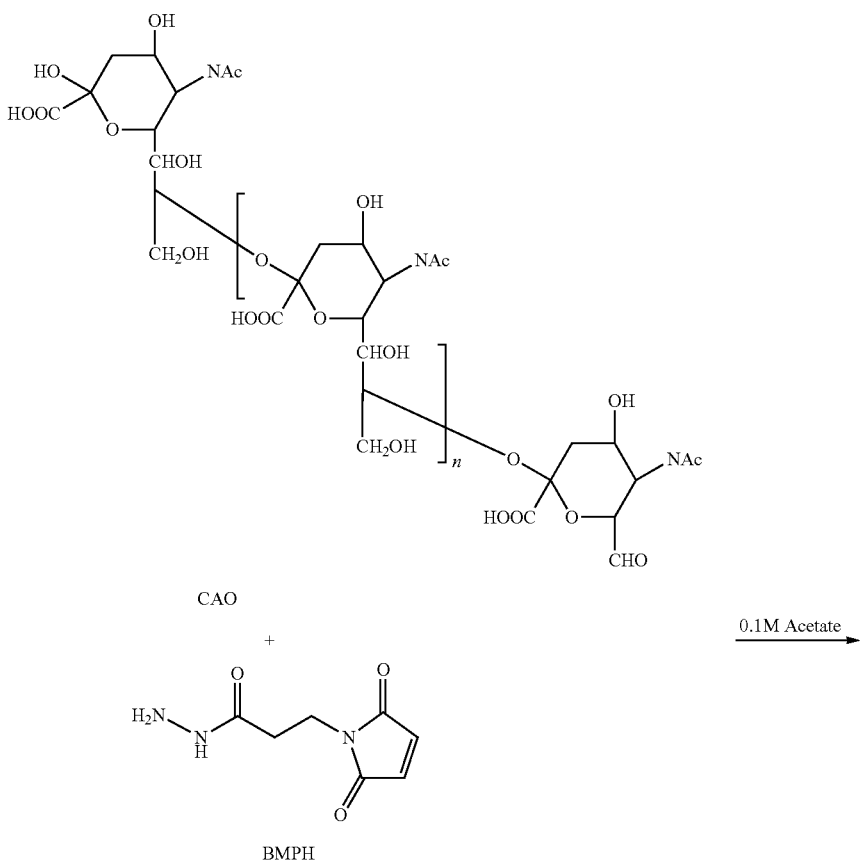

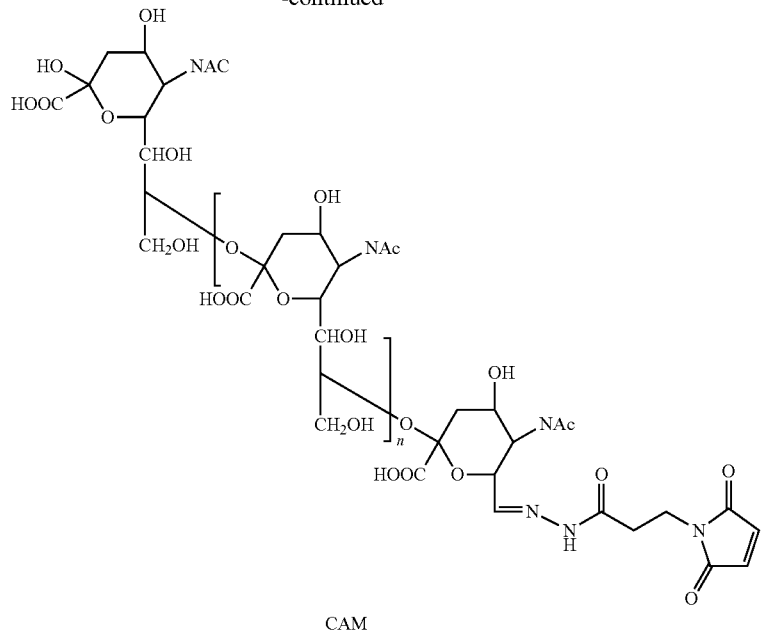

CAM

1.1 Synthesis

Three separate preparations were carried out as follows:

Colominic acid aldehyde (CAO) produced according to WO-A-9222331 (100 mg, $4.4 \times 10^{-6}$ mol) was dissolved into 500 µl 0.1 M sodium acetate, to this 5 molar equivalents of N-[β-maleimidopropionic acid]hydrazide (6.5 mg, $2.2 \times 10^{-5}$ mol) was added. This mixture was then vortex mixed and wrapped in foil and allowed to incubate at 37° C. for 2 h on a rotary mixer. The polymer was then precipitated by the addition of 2 volumes (1.0 ml) of ethanol. The precipitate was collected by centrifugation (13,000 rpm, 2 min) in a bench top microcentrifuge. The supernatant was discarded and the pellet dissolved in 500 µml 0.1 M acetate. This process was repeated a further 2 times and the final pellet dissolved in deionised water and freeze dried overnight.

1.2 Assay for Maleimide Content

In this assay cysteine is reacted with the maleimide on the polymer preventing further reaction with Ellman's Reagent (5,5'-dithiobis(2-nitrobenzoic acid)) which contains a disulphide which forms an intense yellow colour when it is substituted for a thiol not adjacent to an aromatic ring. Thus maleimide content can be calculated by measuring the inhibition of reaction between cysteine and Ellman's reagent assay.

First an initial stock of cysteine at $12 \times 10^{-3}$ M (0.145 mg/ml) was prepared in PBS. In a clean microtitre plate 100 µl volume doubling dilutions from $12 \times 10^{-3}$ M to $0.375 \times 10^{-3}$ M were made from row B to row H. In row A, 100 µl PBS was used as a zero standard. Samples of CA and CA-maleimide (CAM) were prepared at 5 or 10 mg/ml and 100 µl of each sample added to duplicate columns of the cysteine dilutions. In one set, 100 µl PBS without any CA was added as a control. The plate was covered and allowed to incubate at 37° C. for 1 hr. After this time 20 µl of Ellman's reagent (4 mg/ml in PBS) was added to each well and the plate incubated in the dark at room temperature for 15 min. Absorbance was the measured in wells at 405 nm. Standard curves were then plotted for the samples and the amount of maleimide present calculated from inhibition of the signal.

1.3 (Intentionally Omitted)

1.4 Thiolation of FAb and Conjugation to Colominic Acid Maleimide (CAM)

In the first step a thiol group is introduced into a model protein by thiolation of an amine of lysine.

Ovine FAb (anti Desipramine/Norityrptaline, 4 mg, $7.2 \times 10^{-6}$ mol) was dissolved in 0.25 ml PBS+10 mM EDTA; to this was added 0.498 mg 2-iminothiolane (2-IT, Traut's reagent 50 mol equiv $3.6 \times 10^{-6}$ mol) in 0.25 ml of the same buffer. The tube was wrapped in foil and left to incubate stirring end over end for 1 hr. at 37° C.

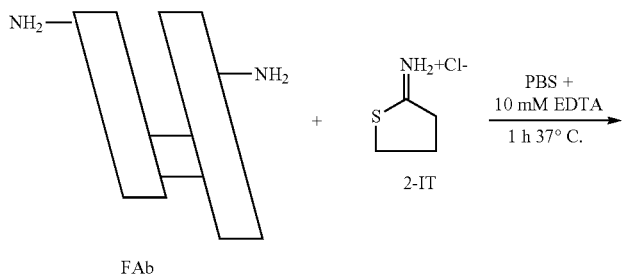

-continued
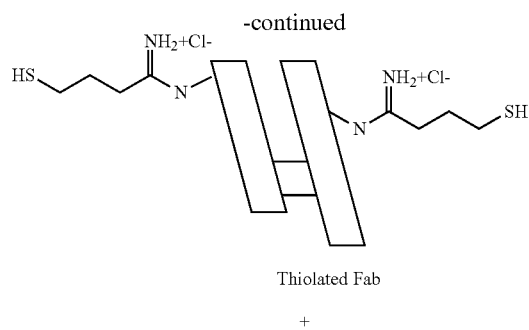
Thiolated Fab
+
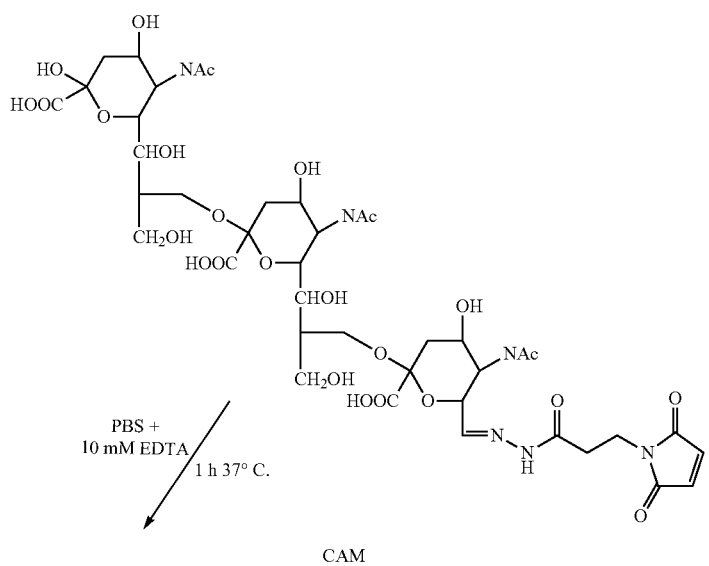
CAM
PBS + 10 mM EDTA / 1 h 37° C.
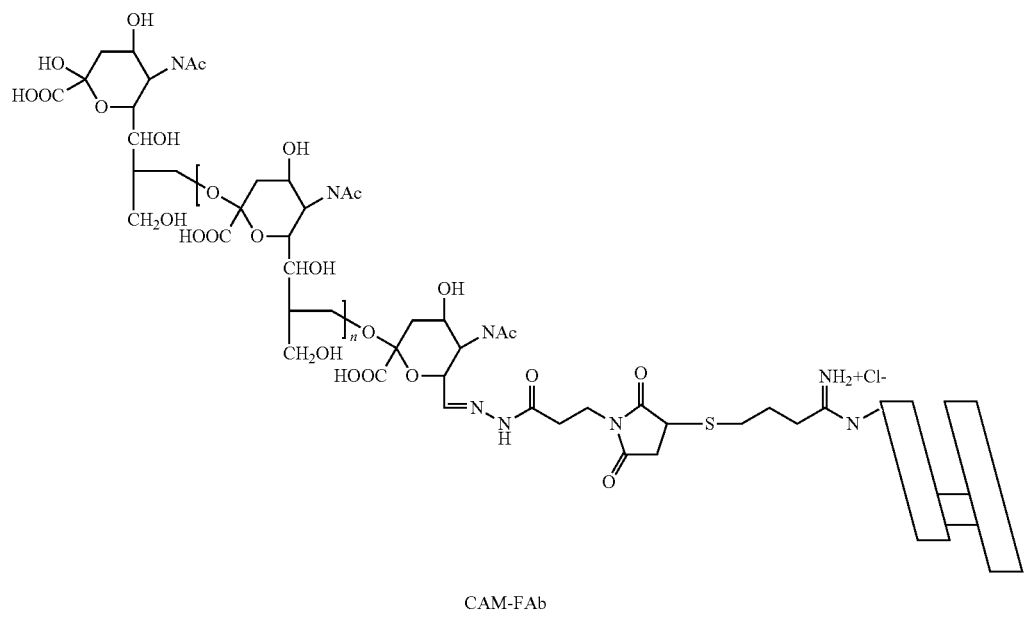
CAM-FAb Thiolated Fab was purified from free 2-IT Traut's reagent by gel filtration (PD-10) and 0.5 ml fractions assayed for presence of protein (BCA assay) or thiol (Ellman's assay). The first eluting peak containing both was pooled and protein and thiols quantified.

1.5 Conjugation of Fab-thiol to CAM

To thiolated FAb (3.6 mg, $6.6 \times 10^{-8}$ mol) in 2 ml PBS/EDTA 22.5 mg CAM was added ($9 \times 10^{-7}$ mol, 15 molar equiv). The tube was sealed and allowed to incubate at 37° C. for 1 h whilst gently mixing. The resulting conjugate was then purified according to accepted protocols to remove free CAM. Both CA and protein content were assayed on the conjugate to calculate conjugation ratio.

Control reactions were carried out with CA as a negative control.

Several batches of CAM-Fab were prepared with various degrees of thiolation but maintaining the 15:1 ratio of CAM:Fab. Results are shown in Table 1 below:

TABLE 1

| Thiol per FAb | Conjugate ratio (CA:Fab) |
|---|---|
| 1 | 0.53:1 |
| 2 | 0.9:1 |
| 5 (triplicate reaction) | 1.925:1 +/− 0.19:1 Fab |
| 10 | 3.51:1 |

FIG. 1 shows an SDS-PAGE gel of the triplicate samples and relevant controls.

1.6 Conclusion

The results show that in all control wells (samples of thiolated FAb) the migration of the sample is similar to that for fresh FAb (below that of the 50 kDa marker) indicating no cross linking of FAb molecules during the process of conjugation. In the replicate lanes there is considerable band broadening with maximum intensity between the 98 and 250 KDa markers which typically indicates an increase in mass which is indicative of a of polysialylated product.

1.7 Conjugation of CAM to β-galactosidase

To *E. coli* β-galactosidase (β-gal) 5.0 mg, $4.3 \times 10^{-8}$ mol) in 1 ml PBS 15 mg CAM was added ($6.59 \times 10^{-7}$ mol, 15 molar equiv). The tube was sealed wrapped in foil and allowed to incubate at room temperature for 1 hr. whilst gently mixing. The resulting conjugate was analysed by SDS page and then purified according to accepted protocols to remove free CAM. Samples were assayed for polymer and protein content as outlined elsewhere.

Control reactions were carried out with CA as a negative control.

1.8 Assay for Enzyme Activity

Standards from 60 μg/ml to 3.75 μg/ml of fresh β-galactosidase were prepared in PBS. Sample of CAM-β-gal were diluted to 60 μg/ml in the same buffer. Enzyme activity of the conjugates was measured as follows: In a microtitre plate, to 100 μl of sample or standard was added 100 μl of All-in-One™ β-gal substrate (Pierce). The plate was incubated at 37° C. for 30 min and absorbance read at 405 nm. A calibration curve was prepared from the standards and the activity of the samples calculated from the equation for the linear regression of the curve.

1.9 Results

Figure 2:
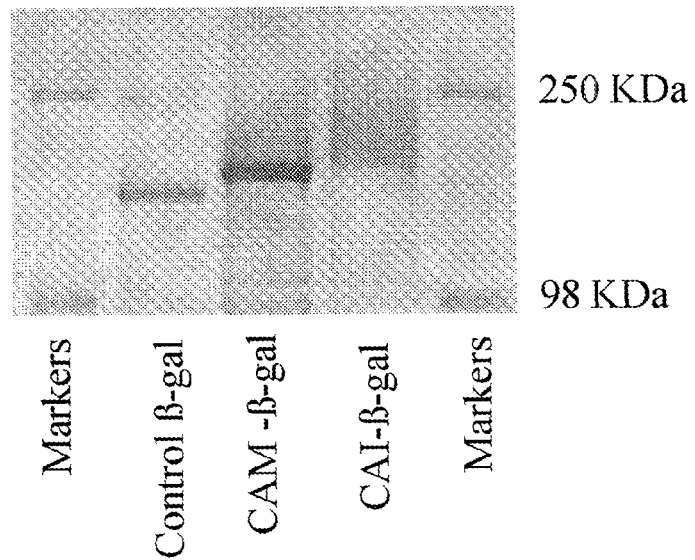
FIG. 2 shows an SDS-PAGE gel of the conjugate of colominic acid iodoacetate (CAI) with β-galactosidase and of CAM with β-galactosidase.

From the protein and polymer assays the conjugation ratio was determined to be 1.23 CAM:1 β-Gal. There was also a corresponding increase in apparent molecular mass from the SDS page of the samples (FIG. 2). Enzyme activity in the purified sample was calculated to be 100.4% compared to the free enzyme.

Example 2

Synthesis Route 2

Step 1 Amination of CA-Aldehyde (CHO)

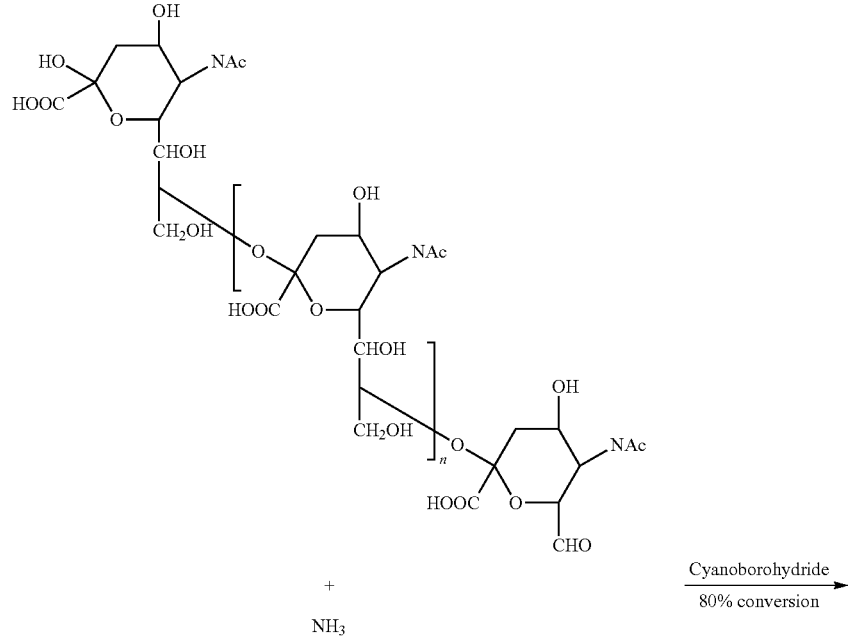

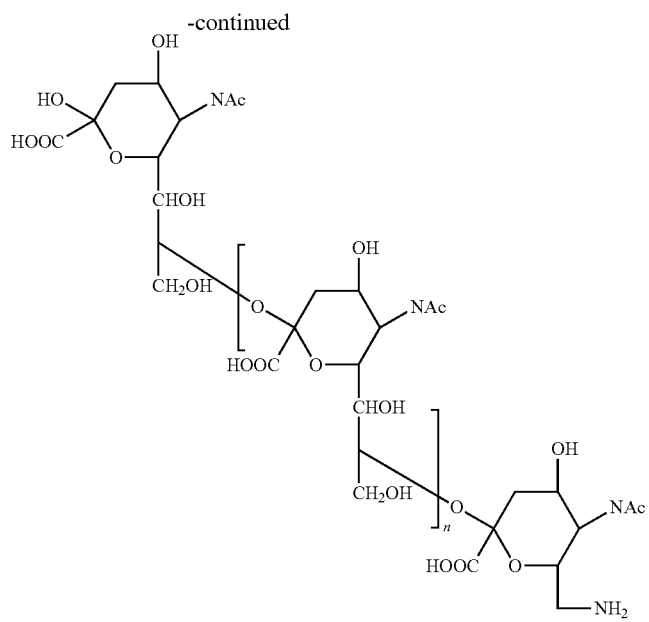
Step 2 Introduction of Maleimide Ring
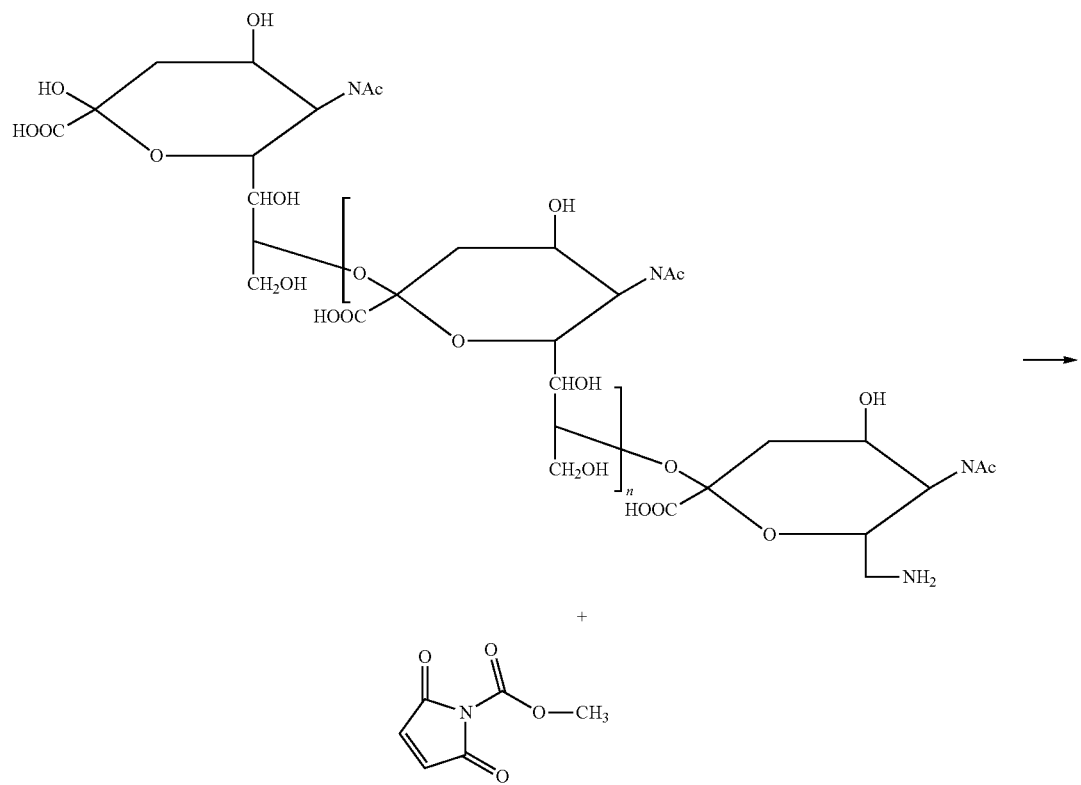

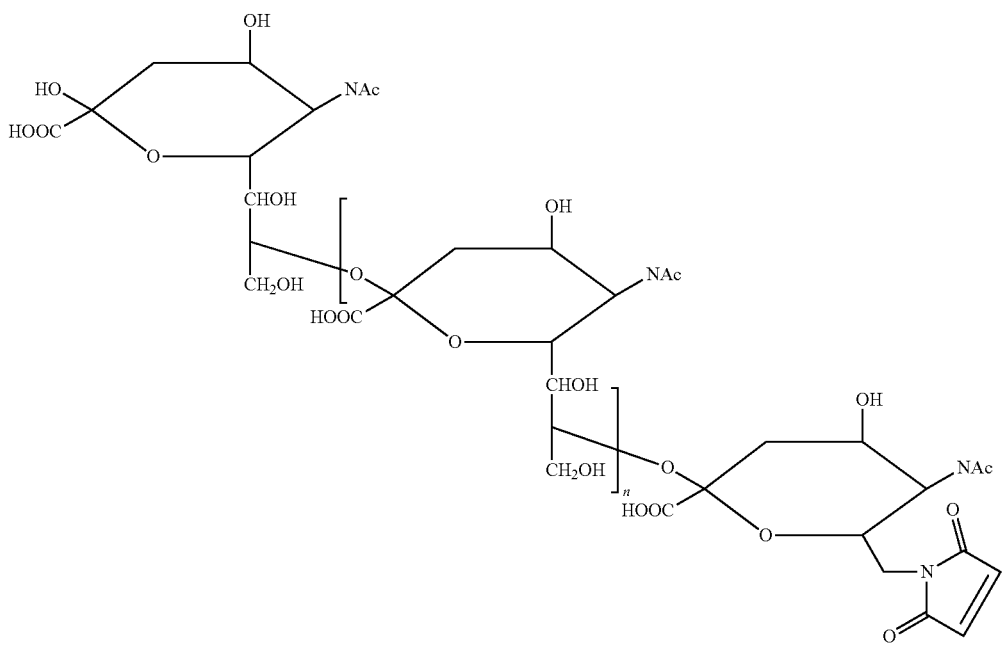

Synthesis

2.1 Step 1 Amination of Oxidised CA

Oxidised colominic acid at (CAO) 10-100 mg/ml was dissolved in 2 ml of deionised water with a 300-fold molar excess of $NH_4Cl$, in a 50 ml tube and then $NaCNBH_3$ (5 M stock in 1 N NaOH(aq) was added at a final concentration of 5 mg/ml. The mixture was incubated at room temperature for 5 days. A control reaction was also set up with colominic acid (A) instead of CAO. Product colominic acid amine derivative was precipitated by the addition of 5 ml ice-cold ethanol. The precipitate was recovered by centrifugation at 4,000 rpm, 30 minutes, room temperature in a benchtop centrifuge. The pellet was retained and resuspended in 2 ml of deionised water, then precipitated again with 5 ml of ice-cold ethanol in a 10 ml ultracentrifuge tube. The precipitate was collected by centrifugation at 30,000 rpm for 30 minutes at room temperature. The pellet was again resuspended in 2 ml of deionised water and freeze-dried.

2.2 Assay for Amine Content

The TNBS (picrylsulphonic acid or 2,4,6-tri-nitro-benzene sulphonic acid) assay was used to determine the amount of amino groups present in the product.

In the well of a microtitre plate TNBS (0.5 μA of 15 mM TNBS) was added to 90 μl of 0.1 M borate buffer pH 9.5. To this was added 10 μl of a 50 mg/ml solution of CA-amide the plate was allowed to stand for 20 minutes at room temperature, before reading the absorbance at 405 nm. Glycine was used as a standard, at a concentration range of 0.1 to 1 mM. TNBS trinitrophenylates primary amine groups. The TNP adduct of the amine is detected.

Testing the product purified with a double cold-ethanol precipitation using the TNBS assay showed close to 90% conversion.

2.3 Maleimidation of CA-Amine

CA-Amine (17 mg) was dissolved in 1 ml deionised water, to this was added 6 mg methoxy-carbonyl-maleimide (MCM). The mixture was left to react at room temperature for 30 min. To the sample 1 100 μl water and 200 μl acetonitrile was added and then incubated at room temperature for 4 h, after which 300 μl $CHCl_3$ was added the tube shaken and the aqueous fraction collected. Then the fraction was purified over a PD-10 column to remove small molecules. The eluate was freeze dried and assayed for maleimide content. The molar concentration of maleimido was 44 mol %.

Example 3

Preparation of Iodoacetate Derivative of Colominic Acid (CAI)

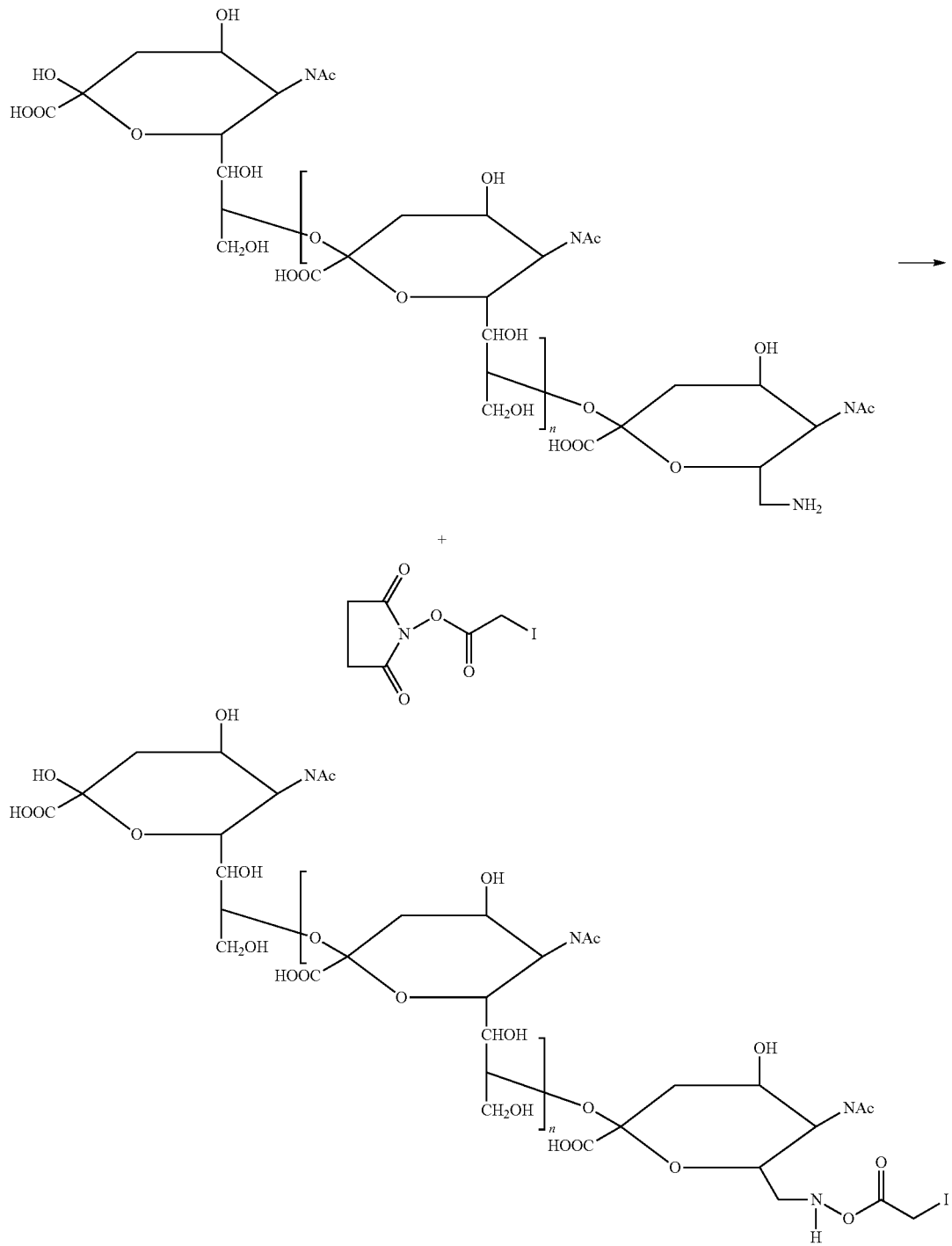

3.1 Synthesis

To 40 mg colominic acid amine (85 mol % amine) as (described in Example 2.1) dissolved in 1 ml of PBS pH 7.4 was added 5 mg of N-succinimidyl iodoacetate (SIA). The mixture was left to react for 1 h at 37° C., after which excess SIA was removed by gel filtration over a 5 ml Hightrap™ Desalting column(AP Bioscience) eluted with PBS. 0.5 ml fractions were collected from the column and samples from each fraction tested for colominic acid content (resorcinol assay) and reactivity with cysteine indicating iodide (Ellman's Assay). Fractions positive for both iodide and CA were pooled.

3.2 Conjugation of CAI to β-galactosidase

To *E. coli* β-galactosidase (5.0 mg, $4.3 \times 10^{-8}$ mol) in 1 ml PBS 15 mg CAI was added ($6.59 \times 10^{-7}$ mol, 15 molar equiv). The tube was sealed wrapped in foil and allowed to incubate at room temperature for 1 hr. whilst gently mixing. The resulting conjugate was analysed by SDS page and then purified according to accepted protocols to remove free CAI. Samples were assayed for polymer and protein content. as outlined elsewhere.

Control reactions were carried out with CA as a negative control. All samples were analysed for β-gal activity as Example 1.8 above.

3.3 Conclusions

Fractions 3-6 were positive for both polymer and iodoacetate and were pooled. The SDS page (4-12% Bis/Tris gel; FIG. 2) showed an increase in apparent molecular mass for samples incubated with the iodoacetamide derivative but not with control polymer. From the protein and polymer assays the conjugation ratio was determined to be 1.63 CAI:1 β-gal. β-gal activity was calculated to be 100.9% for the conjugated sample, compared to the free enzyme.

Example 4

4.1 Synthesis: Non-Reducing End Activation with 4(4-N-maleimidophenyl)butyric acid hydrazide (CA-MBPH) and 3-(2-pyridyldithio)propionyl hydrazide (CA-PDPH)

The preparations were made as follows:
Colominic acid aldehyde (CAO; 22.7 kDa, Camida, Ireland) produced according to WO-A-9222331 (73 mg for MBPH, tube A; 99.3 mg for PDPH; tube B) was dissolved individually into 800 ml 0.1 M sodium acetate (pH 5.5). To tube A 15 mg of MBPH (15:1 linker:CA ratio) dissolved in 200 μl of DMSO was added. To tube B 15 mg (15:1 linker:CA ratio) of PDPH dissolved in 200 of DMSO was added. The pH was adjusted to 5.5 in each case for each reaction vessel. These mixtures were then vortex mixed and wrapped in foil and allowed to incubate at 37° C. for 2 hr. on a orbital mixer. Each polymer solution was purified by gel filtration (PD 10 column) eluting with PBS pH 7.4 and the 1 ml fraction containing CA (by resorcinol assay) collected. These sample were freeze dried overnight and assayed for maleimide content as described in Example 1.2.

4.2 Synthesis: Reducing End Activation with 4(4-N-maleimidophenyl)butyric acid hydrazide (MBPH-CA), (2-pyridyldithio)propionyl hydrazide (PDPH-CA) and N-β-maleimidopropionic acid hydrazide) hydrazide (BMPH-CA)

The preparations were carried out as follows all at molar ratios of 25:1 linker to CA:
Colominic acid (CA; 22.7K; 73 mg for MBPH, tube A; 99.3 mg for PDPH; tube B and 76.6 mg for BMPH; tube C) was dissolved individually into 800 ml 0.1 M sodium acetate (pH 5.5) separately. To tube A, 25 mg of MBPH (dissolved in 200 μl of DMSO), to tube B 25 mg of PDPH (dissolved in 200 μl of DMSO) and to vial C 25 mg of BMPH (dissolved in 200 μl of sodium acetate buffer) were added. The pH of the reaction mixture was adjusted to 5.5. These mixture was then vortex mixed, wrapped in foil and allowed to incubate at 37° C. for 72 h on an orbital mixer. Each polymer solution was purified by gel filtration (PD 10 column) eluting with PBS pH 7.4 and the 1 ml fraction containing CA (by resorcinol assay) collected. These sample were freeze dried overnight and assayed for maleimide content as described in Example 1.2.

4.3 Results

The molar concentration of maleimido was 49.0 and 35.0 mol % for MBPH and PDPH respectively on the non-reducing (highly reactive) end. The molar concentration of maleimido was 41.5, 32.5 and 48.3 mol % for MBPH, PDPH and BMPH respectively on the reducing end (weakly reactive). The values on the reducing end are average of two values in each case.

4.4 Conjugation of β-galactosidase (β-gal) to Maleimide Activated Colominic Acids (Reducing End and Non-Reducing End)

To β-gal (1.0 mg; 1 ml in PBS/EDTA) in separate tubes, a 15 molar excess of each maleimide activated CA (MBPH, PDPH and BMPH on non-reducing or reducing end, from above examples) was added separately. Each tube was sealed and allowed to incubate at 37° C. for 1 h whilst gently mixing. The resulting conjugate was then purified according to accepted protocols to remove free activated polymer. All samples were analysed by SDS PAGE and for β-gal activity as in Example 1.8.

4.5 Results

Figure 3:
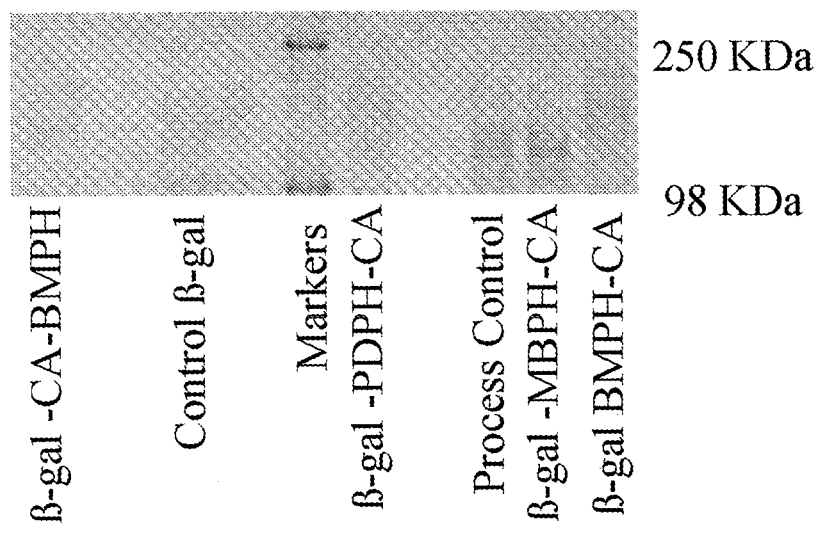
FIG. 3 shows SDS-PAGE gels of conjugates of β-galactosidase with alternate colominic acid derivatives.

The results (FIG. 3) show that in all control wells (with β-gal) the migration of the sample is similar to that for fresh β-gal. In the conjugate lanes there is considerable band broadening with maximum intensity between the 98 and 250 kDa markers which typically indicates an increase in mass which is indicative of a polysialylated-β-gal. β-gal activity was calculated to be 91.0-106% for the conjugated samples.

The invention claimed is:
1. A polysialylated protein, wherein said polysialylated protein is formed by reacting
   a compound comprising a polysaccharide having at least two sialic acid units linked 2.8 and/or 2.9 to one another, and having reducing and non-reducing terminal units and said polysaccharides having a pendant moiety linked to the reducing terminal sialic acid unit which pendant moiety includes a functional group selected from N-maleimide, vinyl sulfone, N-iodoacetamide and orthopyridyl disulfide
   with a protein comprising a thiol group,
   whereby said functional group reacts with said thiol group to form a thioether linkage.
2. The polysialylated protein according to claim 1, wherein said thiol group is that of a cysteine moiety.
3. The polysialylated protein according to claim 1, wherein said thiol group was introduced through a preliminary thiolation step.
4. The polysialylated protein according to claim 3, wherein said preliminary thiolation step comprises reacting an amino group with 2-iminothiolane.
5. The polysialylated protein according to claim 4, wherein said amino group is of a lysine moiety.
6. The polysialylated protein according to claim 1, wherein said pendant moiety further comprises alkylene and/or arylene and/or an oxalkylene and/or oligooxa-alkylene and/or or oligopeptide.

7. The polysialylated protein according to claim 1, wherein said functional group is N-maleimido.

8. The polysialylated protein according to claim 1, wherein said polysaccharide is a polysialic acid.

9. The polysialylated protein according to claim 8, wherein said polysaccharide consists essentially of sialic acid units and said pendant moiety.

10. The polysialylated protein according to claim 8, wherein said polysaccharide has at least 10 saccharide units.

11. The polysialylated protein according to claim 1, wherein said compound has the formula

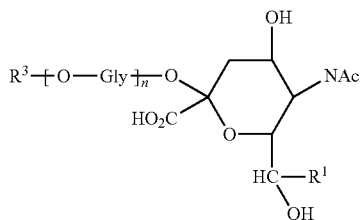

wherein:

$R^1$ is H or —CHOHCH$_2$OH, $R^3$ is —CH$_2$CHR$^4$R$^5$ or —CH(CH$_2$OH)CHR$^4$R)

wherein $R^4$ and $R^5$ together represent =N—NR$^6$ or $R^4$ is H and $R^5$ is —NR$^6$R$^7$ in which $R^6$ is an organic group comprising the said pendant functional group and $R^7$ is H;

O-Gly is a glycosyl (saccharide) group;

n is 1-50; and

Ac is acetyl.

12. The polysialylated protein according to claim 11, wherein each O-Gly is a sialic acid unit.

13. The polysialylated protein according to claim 12, wherein said polysaccharide has at least 10 saccharide units.

14. The polysialylated protein according to claim 1, wherein said polysaccharide has at least 10 saccharide units.

15. The polysialylated protein according to claim 14, wherein said polysaccharide has at least 50 saccharide units.

\* \* \* \* \*